(12) United States Patent
Lasner

(10) Patent No.: US 9,579,166 B2
(45) Date of Patent: Feb. 28, 2017

(54) ROOT CANAL PROBE TOOL AND METHOD OF REMOVING A BROKEN INSTRUMENT FRAGMENT FROM A ROOT CANAL

(71) Applicant: Jeffrey I Lasner, Purchase, NY (US)

(72) Inventor: Jeffrey I Lasner, Purchase, NY (US)

( * ) Notice: Subject to any disclaimer, the term of this patent is extended or adjusted under 35 U.S.C. 154(b) by 245 days.

(21) Appl. No.: 14/454,093

(22) Filed: Aug. 7, 2014

(65) Prior Publication Data

US 2015/0044634 A1 Feb. 12, 2015

Related U.S. Application Data

(60) Provisional application No. 61/958,842, filed on Aug. 7, 2013.

(51) Int. Cl.
*A61C 5/02* (2006.01)
*A61C 1/07* (2006.01)

(52) U.S. Cl.
CPC *A61C 5/026* (2013.01); *A61C 1/07* (2013.01)

(58) Field of Classification Search
CPC ........... A61C 5/026; A61C 5/02; A61C 5/023; A61C 1/07
See application file for complete search history.

(56) References Cited

U.S. PATENT DOCUMENTS

| 4,300,885 A | * | 11/1981 | Khait | A61C 3/16 433/121 |
| 2005/0136375 A1 | * | 6/2005 | Sicurelli, Jr. | A61O 5/026 433/81 |
| 2007/0065773 A1 | * | 3/2007 | Hickok | A61C 5/026 433/119 |
| 2011/0020765 A1 | * | 1/2011 | Maxwell | A61C 17/02 433/119 |

* cited by examiner

*Primary Examiner* — Eduardo C Robert
*Assistant Examiner* — Julianna N Harvey
(74) *Attorney, Agent, or Firm* — Joseph M. Fowler

(57) ABSTRACT

In endodontic therapy, a probe tool is disclosed which enables the removal of a broken file or instrument fragment wedged in a root canal of a tooth. A shank portion of the probe tool is made at least in part from flexible planar sheet material such as stainless spring steel. In a preferred method of use, a dental handpiece transfers oscillations or other cyclical rapid motions through the inventive probe tool to the root canal wall at the juncture with the embedded fragment. A portion of the shank end of the probe tool may be coated with abrasive material. The rapid motions or oscillations imparted to the flexible probe abrade the area where the fragment is wedged and yet minimize collateral damage to adjacent dentinal surfaces. Other types of dental handpieces can be used to transfer vibrational, reciprocating, hammering or circulatory motion to the probe tool when necessary to enhance the effectiveness of the abrading process. Another embodiment of the probe tool comprises a hook type barb to catch the loosened instrument fragment facilitating its removal from a root canal.

8 Claims, 8 Drawing Sheets

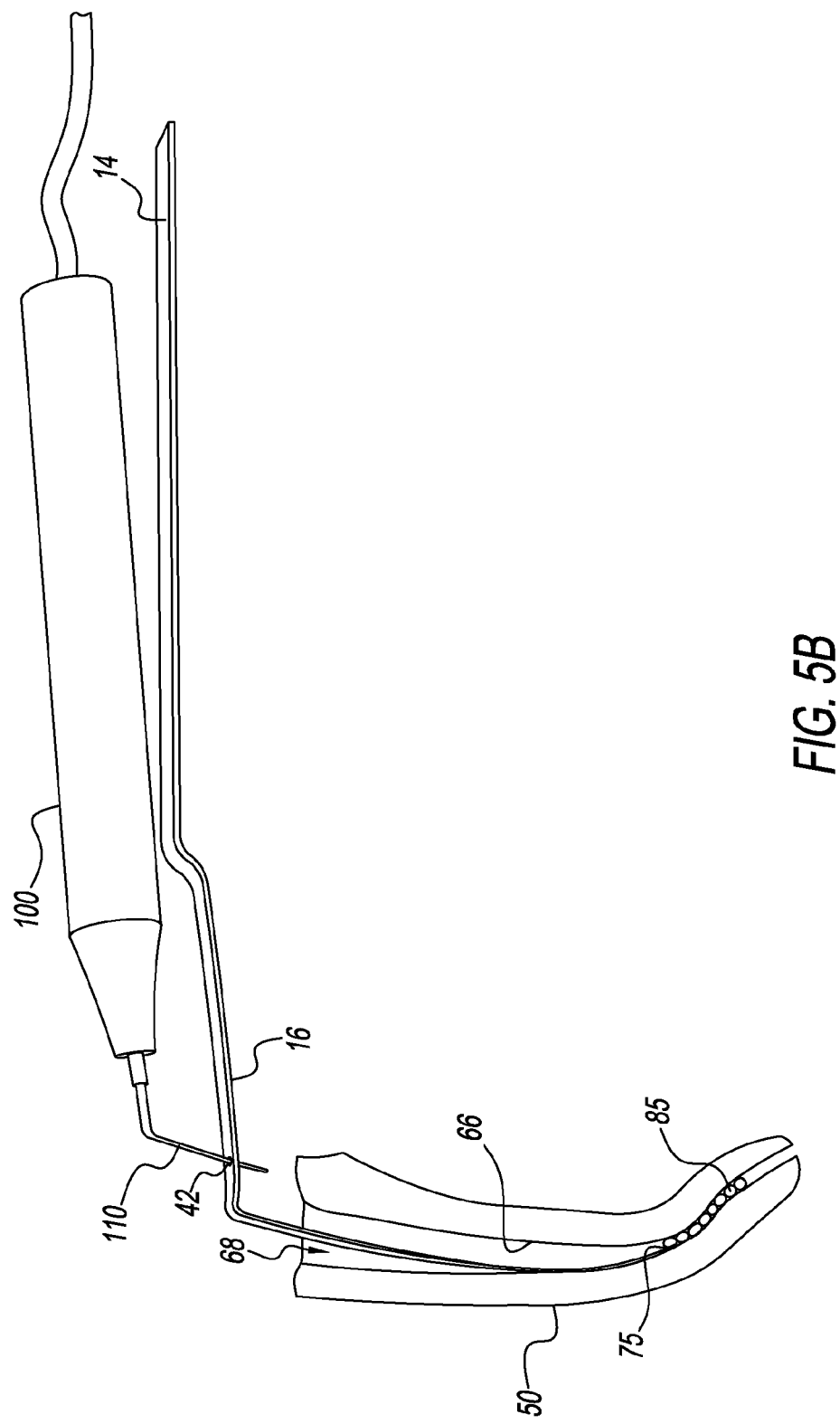

ROOT CANAL PROBE TOOL AND METHOD OF REMOVING A BROKEN INSTRUMENT FRAGMENT FROM A ROOT CANAL

CROSS REFERENCE TO RELATED APPLICATION

This application claims priority to provisional application Ser. No. 61/958,842, filed Aug. 7, 2013.

BACKGROUND OF THE INVENTION

This invention relates to root canal therapy and in particular to the removal of a broken tool or instrument fragment lodged in the pulp chamber or root canal of a tooth.

The pulp chamber contains the pulp tissue which comprises the circulatory, connective and nerve tissue of a tooth. The pulp tissue extends from the jaw bone through one or more root canals inside each tooth to a pulp chamber. It may become necessary for a dentist or endodontic specialist to remove diseased or injured pulp tissue from root canals so that a patient can retain an original tooth in situ. Therefore a primary objective of root canal therapy is to obviate a tooth extraction procedure and its accompanying trauma to surrounding tissue and bone. As part of the therapy, the endodontic clinician removes the pulp material and shapes the root canal prior to inserting filler material in place of the original pulp.

The dental clinician must have fine dexterity and extensive training to perform a pulp extirpation successfully as root canals are very small and the canals themselves are often curved or irregularly configured. In conventional practice the clinician removes at least a portion of the crown of a tooth using a rotary bur or similar instrument to expose openings to the root canal. Small, tapered metal tools or instruments, generally referred to as files, are inserted into a root canal to remove the pulp. Files are available having different metallurgical composition and different mechanical characteristics. A manually operated file is comprised of a handle and a shank, the working end of the tool. The shank is commonly manufactured from very thin wire made from an alloy of nickel-titanium or stainless steel. The wire is helically wound and extends out from the central axis of the handle approximately 5 mm. Files are usually supplied in numbered and colored sets where the number or color on each file handle corresponds to a characteristic of a particular file. Each file in a set may differ slightly in maximum working diameter and each may serve a different specific purpose in the debriding procedure.

In practice a clinician commonly uses the fingers of one hand (usually the thumb and forefinger) to manually insert a file into the exposed opening of a root canal. The file is rotated to engage the pulp tissue while it is simultaneously being moved up and down, carrying out tissue debris and progressively enlarging and shaping the canal space. Other files are designed as reamers to enlarge a canal to a fixed diameter. A typical shank end of a file is 1 mm in diameter at the juncture with the handle and it may taper to a mere 0.2 millimeter in diameter at the tip, or distal end. Such minisculte files are quite prone to break and can become wedged or embedded in the interior dentinal wall of the canal which delays completion of normal therapy. This kind of breakage event requires additional remedial procedures and may ultimately lead to iatrogenic medical complications.

The prior art reveals a number of methods and devices available to the endodontic clinician to recover or remove a broken file. Special mechanical devices for this purpose may be manipulated directly by hand or a device may be attached to a vibratory (ultrasonic) handpiece of a kind available in most dental operatories. There are many commercial vendors and manufacturers of vibratory and ultrasonic dental handpiece devices including, as examples, Sybron Dental Specialties of Orange, Calif., Giulin Woodpecker Medical Instrument Co, Ltd of Guangxi, China, and Satelec Dental Equipment of the Acteon Group in Bordeaux, France.

U.S. Pat. No. 7,080,981 B2, issued to Terauchi in 2006, describes one such device together with accompanying implements for removing a broken instrument from a root canal. One of the Terauchi devices comprises a handle with a fork-shaped cutting end which is used to cut the internal dentin down to expose the head of the embedded broken instrument. Subsequently, after the head is exposed, a second instrument incorporating a stainless steel wire loop is used to effectively "lasso" the broken part enabling it to be withdrawn from the canal space. Other supporting instruments are also described which use tool tips designed for use with an ultrasonic handpiece to abrade or cut the area surrounding the embedded broken tip enabling the use of the wire loop device. While there may be situations in which a clinician could actually catch a broken part in this fashion, it is always desirable to limit destruction of the surrounding dentin as much as possible to better preserve the tooth. If an embedded part is actually free enough to be grabbed, a more conventional and common approach utilizes a very small forceps known as a Steiglitz forceps to grasp a broken piece without having to resort to lassoing.

A patent application publication, U.S. 2003/0157458 A1, by Buchanan describes a number of dental instrument tool tips for performing endodontic procedures. Some of the tips illustrated have abrasive coatings and others have radiused ends to minimize troughs and scratches within the root canal when the tips are used in conjunction with an ultrasonic handpiece. Buchanan discloses tool tips for ultrasonic dental handpieces which are described as less prone to damage a tooth. Inadvertent damage to tooth structures using various kinds of vibratory handpieces is a common and continuing problem in the field of endodontics. Root canals are dimensionally minute, and even well-trained and manually adept clinicians do not have perfect physical control using vibratory instruments within the canal space. As a consequence, abrupt or unintentional movements may cause unwanted removal of dentin material. When scratches and troughs or "ledges" are carved within the canal, small voids are created which are difficult to see even with the aid of dental magnifiers. Therefore it becomes difficult to fully extirpate and sanitize the canal for purposes of complete obturation. If left unfilled, these voids can become repositories for harmful bacteria. In the Buchanan invention, the tool tips are fixedly attached to the ultrasonic handpiece either by a threaded connection or by a mechanical interlock typically used to chuck a driven tool. As such, small erroneous movements by the clinician using an ultrasonic handpiece—even one equipped with Buchanan's less damaging tool shapes—may well induce unwanted material removal and damage to canal surfaces, Another approach to endodontic treatment depicted by Laufer in U.S. Pat. Publ. 2014/0080090 employs what might be called a waterjet in miniature. Laufer shows a dental handpiece which drives a rotary device that creates a vortex-like "micro-tornado" where water mixed with an abrasive is forced through a small cannula to remove pulp and debris and diseased tissue. This device would be new to endodontic therapy and it remains to be seen whether micro-tornadic jets of water-borne slurry can be manipulated accurately enough to perform effectively in standard endodontic clinical practice. If pressures sufficient to remove calcified dentin are achievable through a micro-cannula of this nature, then the same limitations of an ultrasonic handpiece with a rigidly fixed end tool would apply to the micro-tornado device. Slight inadvertent movements by the clinician may have quite adverse consequences for a patient's tooth.

A different unconventional approach, U.S. Pat. No. 7,677,892 B2 (2010) awarded to Alexandrovskiy et al. describes how two electrodes shaped into a small cylinder can be inserted into a root canal to weld the broken piece of a file to the tip of one of the electrodes. The broken file is thereby unified with the electrode and this combination can be withdrawn from the root canal interior. While the concept of welding broken pieces together sounds plausible, in actual practice manipulating an electrode in a curved root canal so that it contacts some deeply embedded file fragment may in many instances be clinically unachievable. At the present time this technique is not commonly used in domestic endodontic practice.

A technique analogous to, and referenced by Alexandrovskiy et al. is used to dissolve a broken file tip electrochemically by the continuous application of electric current. However this electrochemical technique has a tendency to exceed physiologically acceptable temperatures within the confines of a root canal. It is also difficult for the patient in the operatory because it requires a relatively long time to work effectively and can contribute to undesirable toxic aftereffects.

SUMMARY OF THE INVENTION

The present invention describes a method and mechanical device for quickly and efficiently freeing fragments of files or metal instruments that have broken and become wedged in a root canal of a tooth. The method employs a flexible sheet metal probe tool for determining mechanically the location of the broken fragment and, when necessary, freeing the embedded fragment by joining the sheet metal probe to a tool bit attached to a dental handpiece which produces vibratory or reciprocating motion.

What chiefly distinguishes this approach from the prior art is the use of probe tools made from thin, light, highly flexible planar sheet material. In a preferred embodiment, the inventive probe tool is weakly or loosely joined to a tapered tool bit which is a rigidly attached part of a vibratory or reciprocating dental handpiece. This configuration permits "transferred oscillations" to pass from the fixed or rigidly held tool bit through the inventive flexible probe to the junction between the tooth and broken fragment. Flexible probes configured in this manner are far less likely to cause inadvertent damage to internal root canal spaces as they have much greater mechanical forgiveness in comparison to a rigidly fixed oscillating tool bit introduced directly into the root canal space as commonly practiced in endodontic therapy.

Direct contact of a fixed tool bit attached to a dental vibratory handpiece inside a tooth transfers potentially damaging vibration along the entire length of the tool bit or end piece. Physical gouging of a root canal wall can cause zipping or strip perforation as the tool bit bounces across the canal surface. Tissue and bone degeneration may occur in as little as 12 to 15 seconds of direct ultrasonic contact due to the build-up of heat generated by the ultrasonic waves and tool vibrations. To prevent this type of occurrence, and to improve the practice of endodontic therapy, the present invention has been developed which is described more particularly in the following detailed specification. Many of the features of the inventive devices and inventive methods will become apparent when the entire specification is read with reference to the accompanying drawing.

BRIEF DESCRIPTION OF THE DRAWING

FIG. 5B is an elevation with a partial perspective view showing the dental handpiece joined to the inventive probe tool.

DESCRIPTION OF THE DETAILED SPECIFICATION

Figure 1:
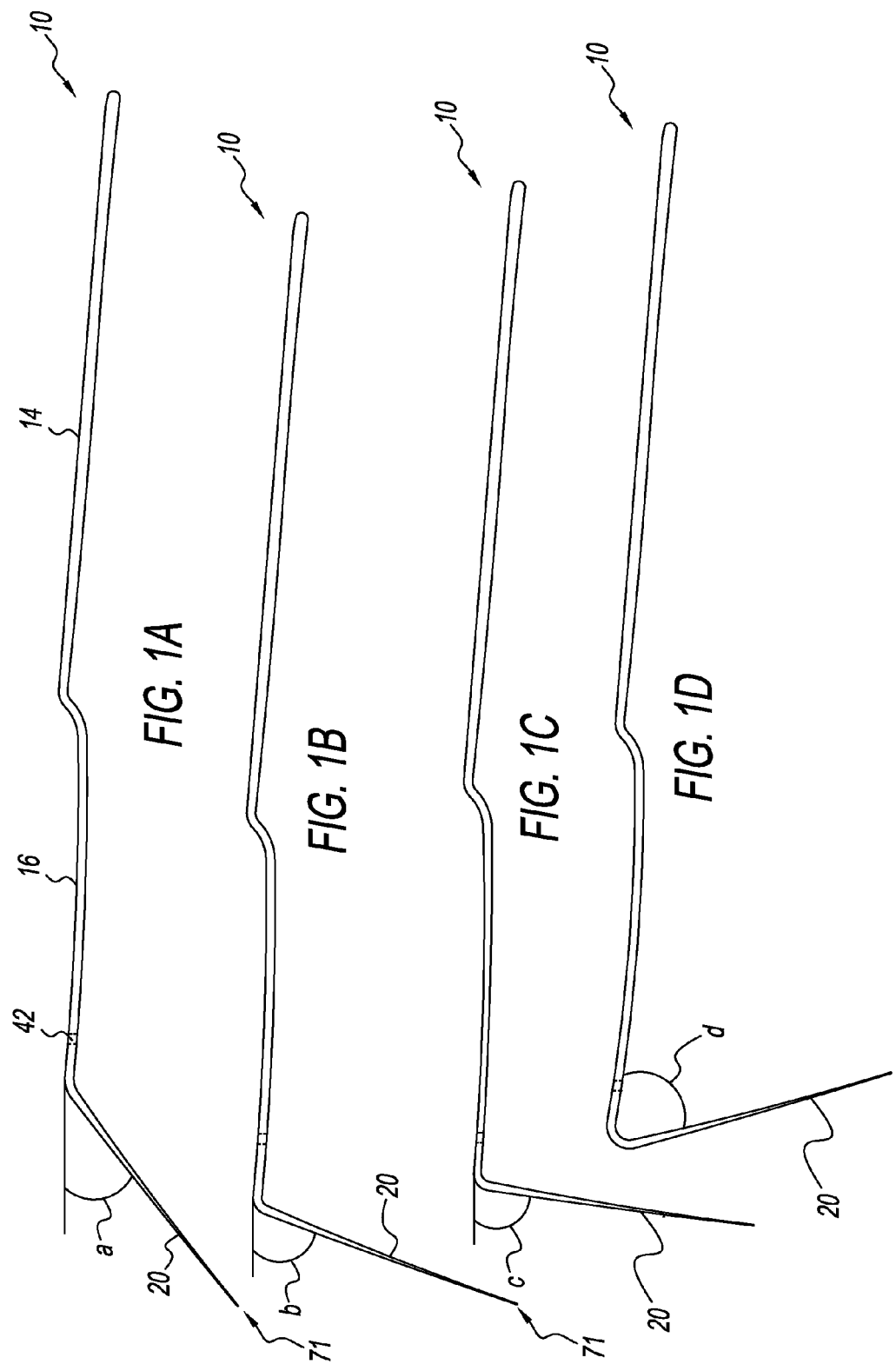
FIG. 1A, FIG. 1B, FIG. 1C and FIG. 1D are elevations depicting a set of the inventive file extraction probe tools in which each different figure designates an end probe which has a different angle with respect to its handle.
Figure 2:
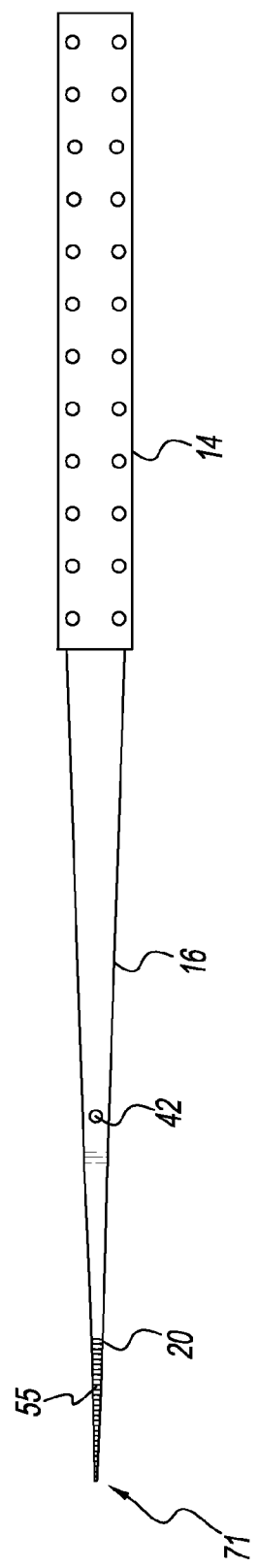
FIG. 2 is a plan view of a single inventive probe tool. The hole or aperture is shown which facilitates the joining of the probe tool with a vibratory or reciprocating dental handpiece. In addition, abrasive particulate coating material is shown on a portion of the flexible end probe although it should be understood that abrasive may or may not be present on one or more sides of the tool depending upon which embodiment of probe tool is chosen for use by the clinician.
Figure 3A:
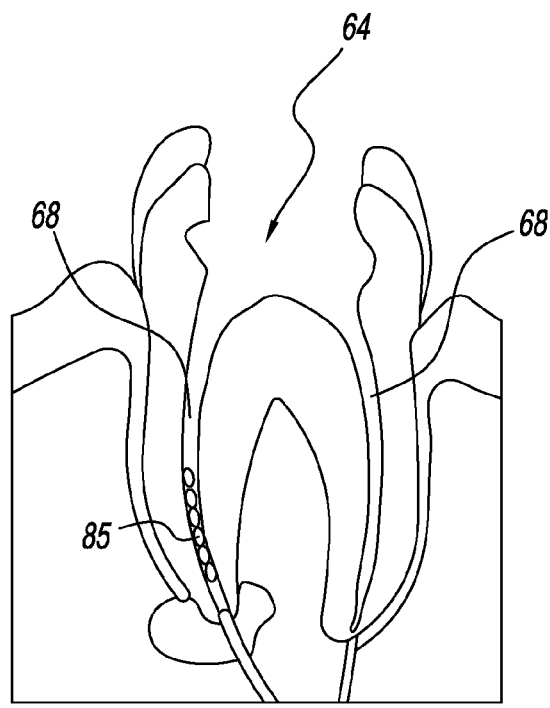
FIG. 3A is an illustration in cross-section of a tooth having a partially removed crown portion exposing debrided root canals.
Figure 3B:
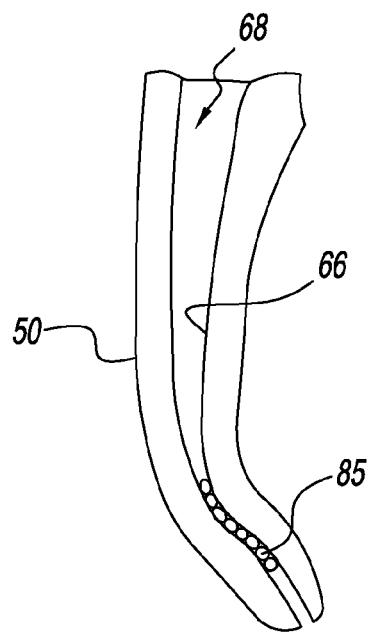
FIG. 3B is an illustration in cross-section of an enlarged portion of one root canal containing a broken file fragment.

With reference to drawing FIG. 3A, a file or instrument fragment 85 is shown wedged within a root canal 68. X-ray or other imaging methods together with direct visual magnifying instruments may be used to locate the broken fragment 85. The dental clinician can then select a probe tool from among a set of inventive probe tools 10, typical examples of which are shown in FIGS. 1A, 1B, 1C, 1D and 2, to physically locate and attempt to free fragment 85.

Each probe tool, generally referred to throughout the drawing by the numeral 10, comprises a handle end 14 and a shank end 16 extending to a point end 71. The shank end 16 extends straight out from handle 14 to a flexible planar body or end probe 20 which terminates after point 71. The overall length of a probe tool 10 is approximately 150 mm (5.9"). End probe 20 is located at the distal end of shank 16 of probe tool 10. The overall length of end probe 20—the flexible planar body—is approximately 32 mm (1.26").

Aperture 42, as seen in FIG. 2, is located on the flat sheet metal along the central axis of shank 16 adjacent the connection or extension to end probe 20. Aperture 42 is typically a round hole approximately 1.58 mm (0.0625") in diameter.

End probe 20 is made from flexible planar sheet material that is arrow-shaped in appearance having its narrow end sized to fit within the root canal of a tooth. In a typical form dimensionally, it is 5 mm (0.197") wide near aperture 42 tapering to less than 1 mm (0.039") in width for most of its length diminishing to 0.5 mm (0.0195") wide or less at its pointed end 71. Probe 20 is approximately 0.6 mm (0.023") in thickness near aperture 42 tapering to 0.32 mm (0.0125") thick at its pointed end 71.

The inventive probe tools are normally manufactured from steel material, more specifically, stainless spring steel alloys that are very flexible and autoclavable so as to be suitable for medical applications. Nickel-titanium or equivalent alloyed metallic materials can also be used for this purpose.

End probes 20 may be angularly offset with respect to each of their handles. This allows the clinician to choose the most comfortable probe tool 10 for a specific task at hand depending upon where a tooth is located in the patient's jaw. In popular configurations, in FIG. 1A, angle a is 45 degrees; FIG. 1B, angle b is 75 degrees; FIG. 1C, angle c is 90 degrees; and FIG. 1D, angle d is 70 degrees.

Figure 4:
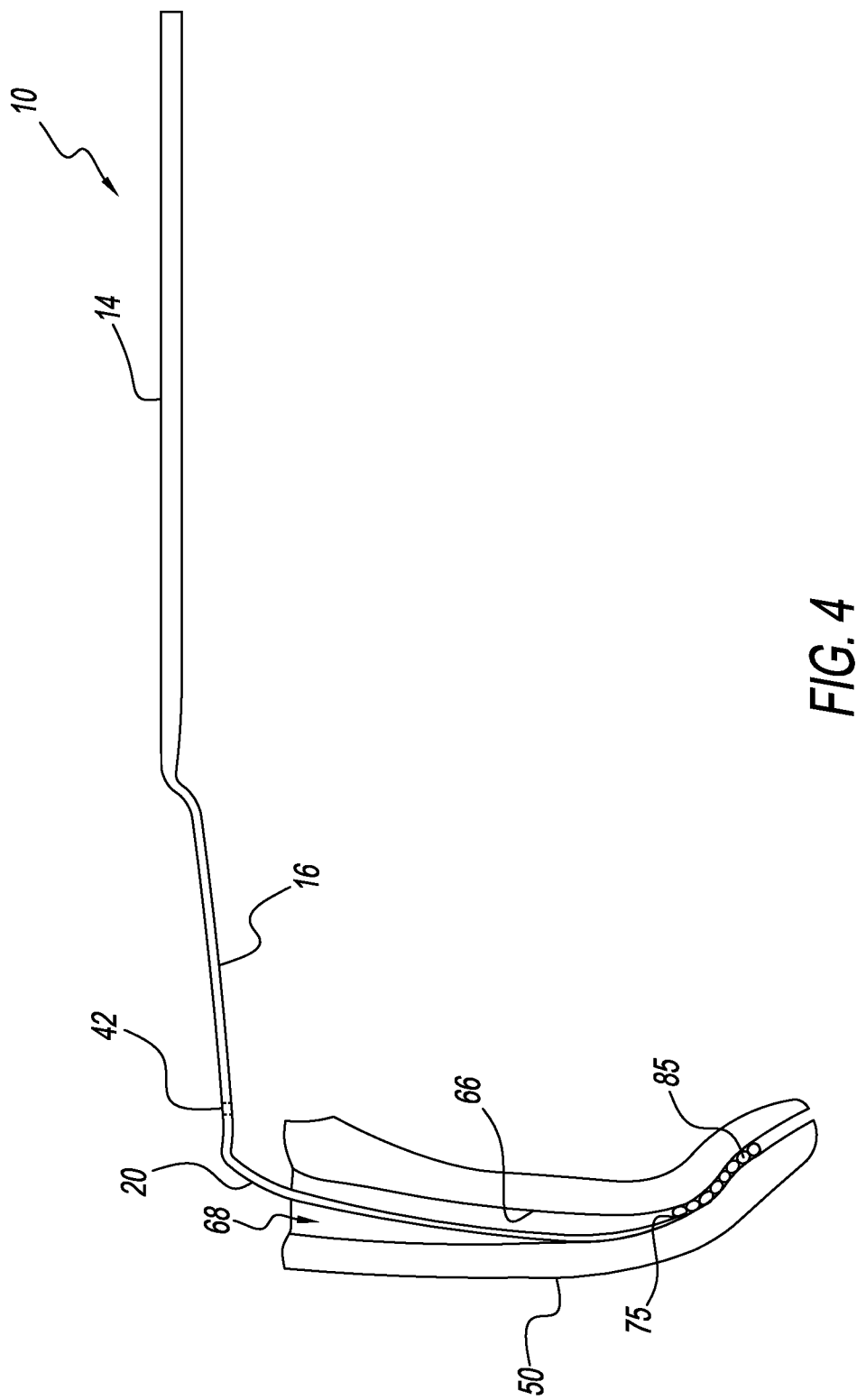
FIG. 4 is an illustration showing a probe tool similar to those shown in FIG. 1 inserted into a root canal. The flexible end probe is shown following the curvature of the canal wall to the point of engagement with a broken file fragment.

A root of a tooth with its crown removed is shown in cross-sectional elevation in FIGS. 3B, 4, 5A and 5B. The root canal 68 is shown exposed in cross-section while simultaneously depicting the internal canal wall 66 and the external surface 50 of the root referred to in dental nomenclature as the "cementum" of the tooth. In use, a particular probe tool 10 is selected by the clinician who inserts the narrow part of the arrow shape—comprising the forward portion of the flexible planar body or end probe 20, through opening 64 (in FIG. 3A) in the crown of the tooth into a root canal 68 (FIG. 4). Probe 20 will flex or bend easily following the contour of a canal wall 66 until it reaches an intersection 75 with fragment 85. If the clinician is unable to dislodge the fragment 85 sufficiently for retrieval using only manual effort, then a second procedure is employed. For purposes of explanation, the location referred to by reference numeral 75 are, at once, an intersection with a fragment, a junction on the dentinal wall and a location for creating a trough as well as defining the region of a trough for the purpose of dislodging a fragment.

Figure 5A:
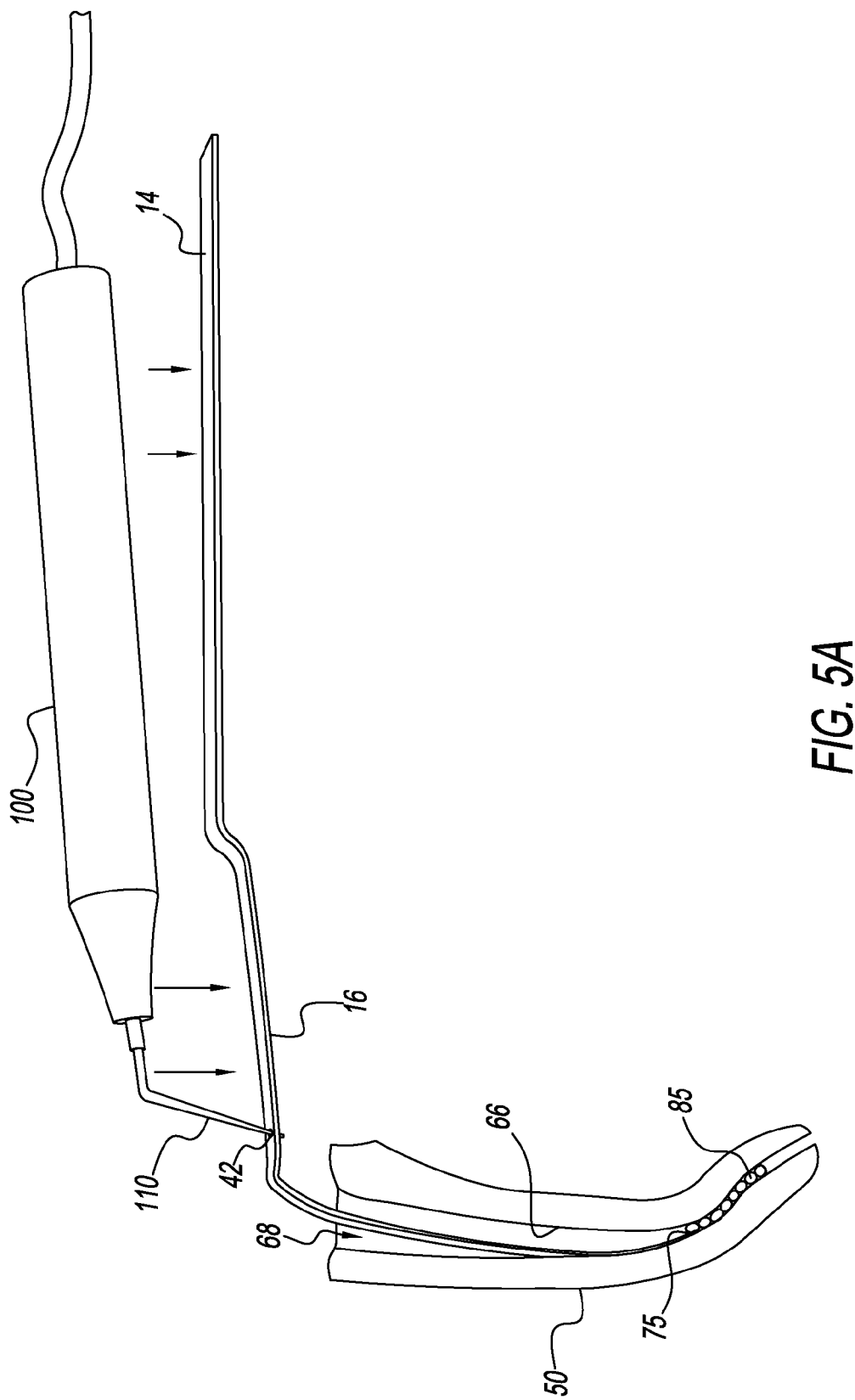
FIG. 5A is an elevation with a partial perspective view of the probe tool and dental handpiece. The handpiece is being moved into position for activation in conjunction with the inventive probe tool.

In this procedure, as depicted in FIG. 5A et seq., tapered tool bit 110, which is rigidly attached to an vibratory or reciprocating handpiece 100, is inserted into aperture 42 located on shank 16 of a probe tool adjacent the proximal end of flexible probe 20. Tapered tool bit 110 fits through aperture 42 and is moved along the tapered surface until the outer surface of the tool bit 110 engages the inner boundary of aperture 42.

Figures 6A, 6B:
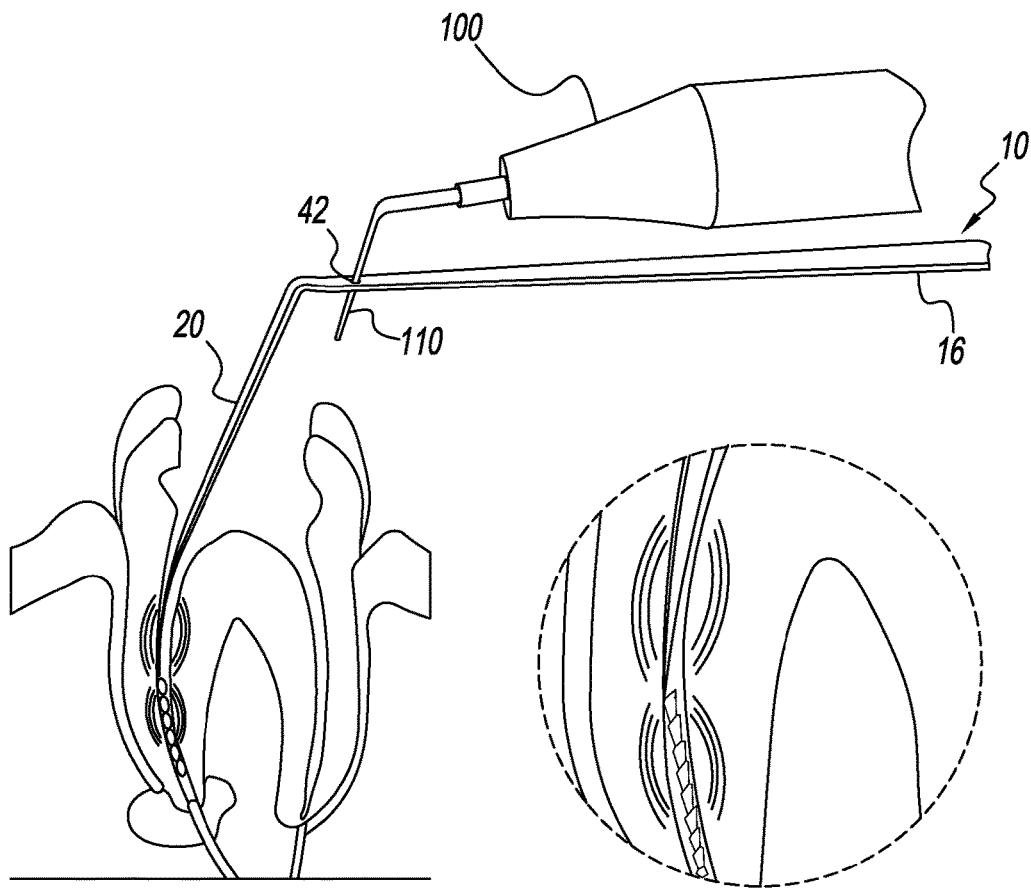
FIG. 6A is a cutaway elevation of a tooth in situ as it is being operated upon using the inventive device joined to a vibratory dental handpiece indicating by the curved line symbols that the end probe and fragment is vibrating from transferred oscillations.
FIG. 6B is an enlarged cutaway view of a portion of a root and root canal area where the probe is transferring oscillations into the wall of the root canal.

In actual practice, the clinician holds handpiece 100 in one hand and holds a probe tool 10 with the other hand while maintaining end probe 20 in contact with the tool bit 110 from the vibratory handpiece. When distal pointed end 71 of probe 20 is correctly positioned at junction 75 on the dentinal wall in the root canal 68, then the vibratory function of handpiece 100 is activated. See FIGS. 6A and 6B.

Figure 7:
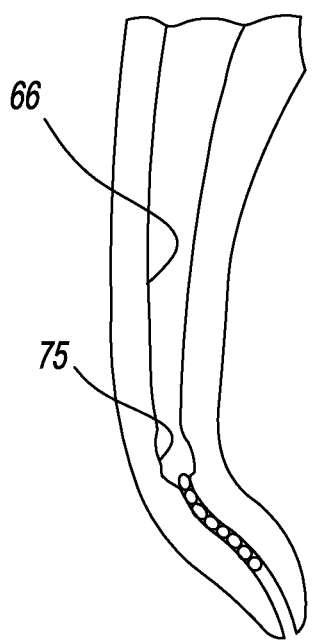
FIG. 7 is an enlarged cutaway view of the root of a tooth showing effective wearing away of the dentinal wall at the location adjacent the top of the broken fragment.
Figure 8:
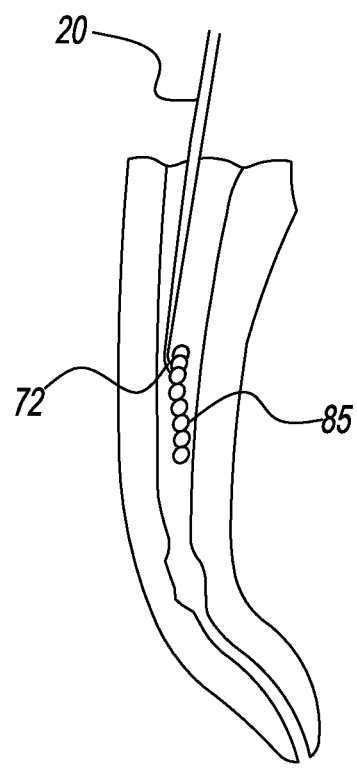
FIG. 8 is an enlarged cutaway view of the root of a tooth depicting a particular embodiment of the probe tool having a barbed end so it can be used as shown for hooking and withdrawing the broken fragment from the root canal.

Abrasive material 55, such as diamond dust, as shown in FIG. 2 embedded as a coating into the surface of end probe 20, causes a wearing away of the dentinal wall 66 at the location 75 creating a trough between the fragment 85 and the wall of the canal 68. The result of the wearing away of dentinal walls is illustrated in FIGS. 7 and 8. The clinician can move the probe 20 up and down to assist the abrading process and thereby minimize unintentional damage to the dentinal walls. The transferred oscillations cause the vibrating tip of probe 20 to promote the loosening of the file fragment 85 from the canal wall 66 by creating a trough in the area of the intersection between the foreign body fragment 85 and the canal wall.

Additionally, the vibrations enable micro-mechanically retentive forces to develop between the flat metal probe 20 and the particulate abrasive 55 as the particulates, typically a grit size ranging from 50 microns (0.05 mm) to 100 microns (0.106 mm), engage flutes of the helically wound file fragment 85. Subsequently, the loosened file can be extracted using a conventional Steiglitz forceps which is designed to function in the small canal space. Alternatively, the clinician can use a barbed or barb shape version of probe tool 10, the end 72 of which is depicted in FIG. 8. The barb 72 can engage projections from a foreign body fragment as it is shown in FIG. 8 hooking onto the edges of the helical flutes of fragment 85 allowing it to be successfully withdrawn from the root canal 68.

While the description of the most commonly used powered dental handpieces has focused on those that produce vibratory motion, other motions are capable of being transferred through this inventive flexible planar probe. In cases where a broken fragment may be trapped in highly calcified root canals, which is not unusual with older patients, a handpiece that more aggressively transfers oscillations to the flexible probe may be appropriate. Power-driven dental handpieces are usually pneumatically driven or electrically driven in a variety of ways. These handpiece devices may impart reciprocating, circular or other cyclical rapid motion to a fixed end tool. As such, in appropriate clinical cases, dental handpieces delivering a variety of different rapid oscillations may be used successfully in conjunction with the inventive probe tool. U.S. Pat. No. 3,921,044 issued to Mcshirley describes an electrically driven dental mallet which imparts hammering motions to gold foil insertions. This type of device is also appropriate for use with the inventive probe when an especially stubborn instrument fragment is encountered. It would be totally inappropriate to penetrate the root canal space with the fixed end of an electrically powered dental mallet. On the other hand, it would be safe and workable for a competent clinician to use the dental mallet in conjunction with the inventive probe as the probe is non-rigid, exceptionally flexible and therefore more easily controlled.

In a further embodiment, not shown in the Drawing, the flexible planar body or end probe 20, extends slightly beyond aperture 42 on shank portion 16. Thus aperture 42 and shank 16 in a shortened form is included in the flexible planar body 20 or end probe portion, however, handle 14 is not present as shank 16 can be used as a reduced in size handle end. In this form, the end probe 20 can be joined to other mechanical or electrical handpieces which could impart rapid oscillations to the flexible planar probe.

In yet another embodiment, not shown in the Drawing, edges along portions of the perimeter of the flexible planar body or end probe 20 surrounding point end 71 include serrations to enhance the ability of the probe to engage the canal wall 66 and widen the trough region 75.

What is claimed is:

1. An endodontic probe tool comprising:
   a handle end and a shank end extending to a point end having a flexible flat planar body sized to fit within the root canal of a tooth,
   said shank end having an aperture adapted to receive into physical contact an end tool attached to a dental handpiece,
   said dental handpiece selectively capable of producing rapid oscillations and transferring said oscillations by means of said end tool through physical contact with said flexible flat planar body to the dentinal walls of the tooth.

2. The endodontic probe tool of claim 1 in which a portion of said flexible flat planar body is abrasively coated.

3. The endodontic probe tool of claim 1 in which said flexible flat planar body is composed of stainless steel.

4. The endodontic probe tool of claim 1 in which at least a portion of the edge along the perimeter of the flexible flat planar body is serrated.

5. The endodontic probe tool of claim 1 in which said flexible flat planar body is composed of nickel titanium alloy.

6. The endodontic probe tool of claim 1 in which said point end forms a barb shape.

7. A method of removing a broken instrument fragment contained within a root canal of a tooth comprising the steps of:
   selecting a probe tool having a flexible flat planar body having an aperture located on a flat portion of said body adapted to receive into physical contact an end tool attached to a dental handpiece and inserting the forward portion of said flat planar body into the root canal of a tooth,
   intersecting the broken instrument fragment with said forward portion at the root canal wall,
   locating an end tool attached to a dental handpiece so as to engage said aperture in said probe tool,
   activating said dental handpiece causing rapid mechanical oscillations to transfer through said end tool to said probe tool and said planar body causing an abrasion of the root canal wall thereby freeing the broken instrument fragment.

8. The method according to claim 7, wherein a flexible flat planar probe tool having a barb shape engages and withdraws a broken instrument fragment.

* * * * *